United States Patent [19]
Blankenburg et al.

[11] Patent Number: 6,107,397
[45] Date of Patent: Aug. 22, 2000

[54] AQUEOUS COPOLYMER DISPERSIONS OF WATER-SOLUBLE MONOMERS WITH N-VINYL GROUPS AND HYDROPHOBIC MONOMERS

[75] Inventors: Rainer Blankenburg, Stuttgart-Feuerbach; Volker Schehlmann, Römerberg; Karl Kolter, Limburgerhof, all of Germany

[73] Assignee: BASF Aktiengesellschaft, Ludwigshafen, Germany

[21] Appl. No.: 09/042,744

[22] Filed: Mar. 17, 1998

[30] Foreign Application Priority Data

Mar. 24, 1997 [DE] Germany .............. 197 12 247
Nov. 3, 1997 [DE] Germany .............. 197 48 545

[51] Int. Cl.⁷ .............. C08L 39/04; C08L 39/06
[52] U.S. Cl. .............. 524/813; 524/812; 524/808
[58] Field of Search .............. 524/808, 813, 524/812, 816

[56] References Cited

U.S. PATENT DOCUMENTS

| | | | |
|---|---|---|---|
| 3,032,539 | 5/1962 | Schuller et al. | 260/85 |
| 3,862,915 | 1/1975 | Fried et al. | 260/29 |
| 4,167,439 | 9/1979 | Killam | 162/163 |
| 4,520,179 | 5/1985 | Barabas et al. | 526/212 |
| 5,122,582 | 6/1992 | Potthoff-Karl | 526/81 |
| 5,319,041 | 6/1994 | Zhong et al. | 526/73 |
| 5,426,163 | 6/1995 | Buehler et al. | 526/207 |
| 5,506,315 | 4/1996 | Meyer et al. | 526/89 |
| 5,521,267 | 5/1996 | Giencke et al. | 526/201 |
| 5,591,799 | 1/1997 | Bott et al. | 524/555 |
| 5,679,738 | 10/1997 | Bufford et al. | 524/555 |
| 5,912,294 | 6/1999 | Schade | 524/501 |

FOREIGN PATENT DOCUMENTS

| | | |
|---|---|---|
| 2178328 | 6/1995 | Canada . |
| 795567 | 9/1997 | European Pat. Off. . |
| 93/15120 | 8/1993 | WIPO . |
| WO 9405855 | 3/1994 | WIPO . |

*Primary Examiner*—David W. Wu
*Assistant Examiner*—Kelechi C. Egwim
*Attorney, Agent, or Firm*—Keil & Weinkauf

[57] ABSTRACT

An aqueous copolymer dispersion is prepared by free-radical emulsion co-polymerization of a monomer mixture of i) from 10 to 70% by weight of at least one nonionic monomer A having a water-solubility of more than 60 g/l at 25° C., and being selected from the group consisting of N-vinyllactams having from 6 to 8 carbon atoms, N-vinylformamide and N-methyl-N-vinylacetamide, ii) from 30 to 90% by weight of at least one monoethylenically unsaturated hydrophobic monomer B having a water-solubility of less than 60 g/l at 25° C., and optionally further comprising iii) up to 5% by weight of at least one monoethylenically unsaturated monomer C which has at least one ionic and/or ionizable functional group, iv) up to 10% by weight of at least one monomer D which has at least 2 ethylenically unsaturated bonds, v) up to 20% by weight of at least one further monoethylenically unsaturated monomer E, which is different from the monomers A and C, and has a water-solubility of >60 g/l at 25° C., in the presence of a water-soluble polymerization initiator in water or an aqueous solvent.

22 Claims, No Drawings

AQUEOUS COPOLYMER DISPERSIONS OF WATER-SOLUBLE MONOMERS WITH N-VINYL GROUPS AND HYDROPHOBIC MONOMERS

The present invention relates to a process for preparing aqueous copolymer dispersions by free-radical aqueous emulsion polymerization of monomer mixtures comprising essentially nonionic water-soluble monomers with N-vinyl groups (monomers A) and hydrophobic monomers.

Copolymers of water-soluble, N-vinyl-functional monomers and hydrophobic monomers are known in principle. In general they are prepared by free-radical solution polymerization in an organic solvent, such as an aliphatic alcohol of 1 to 4 carbons, or in alcohol/water mixtures (see for example U.S. Pat. No. 4,520,179, U.S. Pat. No. 5,319,041 or EP-A 418 721). The abandonment of organic solvents, however, is of fundamental interest not least on grounds of cost and of better environmental compatibility.

The replacement of organic solvents by water as solvent is possible to a limited extent in connection with the free-radical copolymerization of water-soluble, N-vinyl-functional monomers and hydrophobic comonomers. For instance, DE-A 22 18 935 describes the free-radical copolymerization of N-vinylpyrrolidone with up to 30% by weight, preferably up to 15% by weight, of hydrophobic monomers, in the manner of an aqueous solution polymerization. In the case of the aqueous solution polymerization of N-vinyllactams that is described in WO 93/18073 the proportion of hydrophobic monomers is likewise restricted to less than 30% by weight, based on the overall amount of monomers to be polymerized.

It ought in principle to be possible to obtain polymers having a higher content of hydrophobic monomers by the method of free-radical aqueous emulsion polymerization. DE-A 41 39 963 and WO 93/15120, however, mention that the free-radical aqueous emulsion polymerization of monomer mixtures containing more than 10% by weight of vinylpyrrolidone leads to unstable dispersions of high viscosity which have a tendency to separate and which, furthermore, are difficult to reproduce. For this reason, when preparing aqueous polymer dispersions containing relatively large amounts of water-soluble, N-vinyl-functional monomers in copolymerized form, free-radical solution polymerization in an alcoholic solvent with subsequent exchange of the solvent for water is avoided (see, for example, DE-A 41 39 963). In addition to the above disadvantages when using alcohols as solvent it should be borne in mind that alcohols, unlike water, intervene as regulators in the free-radical polymerization reaction, and so copolymers of high molecular weight are not obtainable by this route.

WO 93/15120 describes emulsion graft copolymers obtainable by free-radical grafting of hydrophobic monomers onto water-soluble homo- or copolymers formed from water-soluble, N-vinyl-functional monomers in aqueous emulsion.

U.S. Pat. No. 4,167,439 describes nonionic copolymers containing in copolymerized form from 5 to 30% by weight of N-vinylpyrrolidone, from 15 to 60% by weight of acrylamide and from 30 to 70% by weight of methyl methacrylate, which are obtainable by free-radical polymerization in an aqueous solvent. These copolymers are known as microemulsion polymers, with particle sizes preferably in the range from 0.05 to 0.08 μm. The use of relatively large amounts of acrylamide in polymerization reactions in an aqueous medium, however, is not without its problems, since the content of unpolymerized acrylamide in the dispersions that can be obtained by this method is relatively high, and this compound is suspected of being carcinogenic or at least allergenic.

DE-A 43 42 281 describes the polymerization, in aqueous emulsion, of monomer mixtures consisting essentially of N-vinylcaprolactam. Since the solubility of polymers based on N-vinylcaprolactam, especially at the preferred contents of copolymerized N-vinylcaprolactam of above 90% by weight, shows a decrease in water as the temperature rises, the polymerization, although it takes place in aqueous emulsion, leads to polymers which do not give clear solutions in water. Polymers of this kind are not a subject of the present invention.

It is an object of the present invention, therefore, to provide a process for preparing copolymers from water-soluble monomers A containing an N-vinyl group and from at least 30% by weight of hydrophobic monomers B, by free-radical polymerization of the monomers B in a reaction medium consisting essentially of water.

We have found that this object can be achieved by conducting the polymerization as a free-radical aqueous emulsion polymerization using a water-soluble polymerization initiator.

The present invention accordingly provides a process for preparing an aqueous copolymer dispersion by free-radical aqueous emulsion polymerization of ethylenically unsaturated monomers comprising i) from 10 to 70% by weight of at least one nonionic monomer A having a water-solubility of more than 60 g/l at 25° C. and containing an N-vinyl group, ii) from 30 to 90% by weight of at least one monoethylenically unsaturated hydrophobic monomer B having a water-solubility of less than 60 g/l at 25° C. and, if desired, iii) from 0 to 5% by weight of at least one monoethylenically unsaturated monomer C which has at least one ionic and/or ionizable functional group, iv) from 0 to 10% by weight of at least one monomer D which has at least 2 ethylenically unsaturated bonds, v) from 0 to 20% by weight of at least one further monoethylenically unsaturated monomer E, which is different from the monomers A and C, and has a water-solubility of >60 g/l at 25° C., which comprises using a water-soluble polymerization initiator. The percentages by weight given hereinbelow for the monomers A to E relate always to the overall amount of monomers to be polymerized.

The present invention also provides the polymer dispersions obtainable by the process of the invention.

In principle the initiators used are those whose solubility in water is so great that the amount of initiator used is completely dissolved within the respective reaction medium. Preferred polymerization initiators include water-soluble azo compounds, such as 2,2'-azobis[2-(2-imidazolin-2-yl)propane, 2,2'-azobis(2-amidinopropane) and their acid addition salts, especially the hydrochlorides, acetates or (hydrogen)sulfates, 4,4'-azobis(4-cyanovaleric acid) and the alkali metal or ammonium salts thereof, especially the sodium salts, or 2-(carbamoylazo)isobutyronitrile. They further include water-soluble peroxides and hydroperoxides, such as tert-butyl hydroperoxide, tert-amyl hydroperoxide, cumene hydroperoxide, pinane hydroperoxide, peroxodisulfuric acid and its salts, especially its alkali metal or ammonium salts, and hydrogen peroxide. These peroxides and hydroperoxides can be employed alone or, preferably, together with a reducing agent, such as a salt of hydroxymethanesulfinic or ascorbic acid, or a transition metal compound which is able in aqueous solution to exist in various oxidation states, examples being iron(II) salts or copper(II) salts (known as redox initiator systems). Particularly preferred initiators are the abovementioned water-soluble azo compounds, especially those present in salt form or able to form salts, the salts of peroxodisulfuric acid, and hydrogen peroxide, the latter initiators preferably being used together with iron(II) salts or copper(II) salts.

The amount of initiator used for the polymerization lies preferably within the range from 0.02 to 15 mol-%, in particular from 0.05 to 10 mol-%, and, with very particular preference, from 0.1 to 3 mol-%, based on the overall amount of the monomers A to E that are to be polymerized. When the abovementioned azo compounds are used as inititiators the amount of initiator is preferably below 1 mol-%, whereas in the case of the peroxides and hydroperoxides as polymerization inititiators larger amounts are preferably used. The polymerization initiator is preferably supplied to the polymerization reaction in dissolved or diluted form. Suitable solvents are the abovementioned $C_1$–$C_4$ alcohols and/or water, preference being given to the use of water as sole solvent and/or diluent. The initiator content of such solutions is preferably within the range from 0.2 to 20% by weight and, in particular, from 0.5 to 10% by weight.

The initiator can be included in the initial polymerization mixture or can be supplied at the rate at which it is consumed. In a preferred embodiment of the present invention at least 70%, in particular at least 80% and, with very particular preference, at least 90% of the initiator are supplied continuously to the polymerization reaction in the form of an aqueous or aqueous-alcoholic solution. A small amount of initiator, preferably at least 1%, in particular at least 2% and, with very particular preference, at least 5% of the initiator, is included in the initial charge to the reactor in order to start the polymerization reaction.

The reaction medium used for the free-radical emulsion polymerization is water with a content of generally not more than 20% by weight, preferably not more than 10% by weight and, in particular, not more than 5% by weight, based on the reaction medium, of one or more $C_1$–$C_4$ alcohols, such as methanol, ethanol, n-propanol, n-butanol or isobutanol. Particular preference is given to the use of water as sole reaction medium. The polymerization is usually conducted at an almost neutral pH, preferably in the range from 5 to 9. This pH can be adjusted or maintained by adding a base, such as ammonia or sodium hydroxide, or an acid, such as hydrochloric or sulfuric acid. Alternatively, the polymerization can be conducted in the presence of an appropriate buffer, examples being ammonium hydrogen carbonate, hydrogen phosphate, borate, acetate, citrate, succinate, glycinate or phthalate. Preference is given to organic buffer substances, but especially to ammonium hydrogen carbonate.

The monomers that are to be polymerized can be introduced into the reactor at the start in the aqueous reaction medium (batch technique). Polymerization is preferably carried out, however, by a feed technique. By this is meant that the majority, in particular at least 70% and with very particular preference from 75 to 90%, of the monomers to be polymerized, is metered into the initial polymerization mixture in the form, if desired, of an aqueous or aqueous-alcoholic solution or as an aqueous emulsion.

In the case of a feed technique the polymerization initiator can be either included in the initial charge to the reaction vessel or metered into the initial polymerization mixture in the manner described above. The initiator is preferably added continuously and in parallel with the addition of the monomers. Very particular preference is given to the initial introduction of the abovementioned portions of the monomers and of the initiator in the aqueous or aqueous-alcoholic reaction medium, which is then brought to reaction temperature. The monomers are generally added over a period of from 0.5 to 14 hours, preferably from 1 to 12 hours and, with very particular preference, from 2 to 10 hours. The addition of the initiator is made over the same, or preferably a longer, period.

The reaction temperature is usually within the range from 60 to 90° C. but may be up to 130° C. The reaction can be carried out at atmospheric pressure or, if higher temperatures are used, under its own vapor pressure or under the superatmospheric pressure resulting from the use of an inert gas. Nitrogen in particular is suitable as an inert gas.

The polymerization can also be initiated by means of high-energy radiation, such as γ radiation, or can be carried out as a photopolymerization; that is, one initiated by visible light or UV light in the presence of appropriate, water-soluble photoinitiators. Particularly suitable photoinitiators include water-soluble derivatives of acetophenone, benzophenone or thioxanthone, these derivatives generally carrying functional groups which enhance their solubility in water, such as OH, carboxyl, nitro or amino groups.

The polymerization proper is preferably followed by a postpolymerization to complete the monomer conversion. This means that, following the addition of the monomers/of the polymerization initiator, further, free-radical-forming initiators are supplied to the initial polymerization mixture and, if desired, the temperature of the reaction mixture is raised to temperatures above the actual polymerization temperature. Suitable initiators for the postpolymerization are the abovementioned initiators and also percarbonates or peroxo esters. The peroxides and/or hydroperoxides mentioned are preferably employed together with a reducing agent and/or with a transition metal (see above). Postpolymerization generally follows on directly from, or within a period of up to 4 hours after, the end of the addition of monomer/initiator. The initiator required for the postpolymerization can be added all at once or over a period of up to 10 hours. A further possibility is to add two or more initiators in succession for the postpolymerization.

The resulting dispersions, following the polymerization and—or instead of—a postpolymerization, can be subjected to a physical after treatment: for example, a steam distillation or a stripping operation with an inert gas such as nitrogen. This removes steam-volatile impurities, such as residual monomers, from the dispersion.

The polymers obtained by the polymerization process of the invention generally have relatively high molecular weights. Should lower molecular weights be desired, they can be established by adding a regulator to the initial polymerization mixture.

Examples of suitable regulators are aldehydes, such as formaldehyde, acetaldehyde, propionaldehyde, n-butyraldehyde and isobutyraldehyde, formic acid, ammonium formate, hydroxylammonium sulfate and hydroxylammonium phosphate. It is also possible to use regulators containing sulfur in organically bonded form. Examples of such regulators are di-n-butyl, di-n-octyl or diphenyl sulfide, diisopropyl, di-n-butyl, di-n-hexyl or diacetyl disulfide and di-tert-butyl trisulfide. The regulators preferably contain sulfur in the form of SH groups. Examples of regulators of this kind are n-butyl, n-hexyl or n-dodecyl mercaptan. Particular preference is given to water-soluble, sulfur-containing polymerization regulators, such as hydrogensulfites, disulfites and compounds such as ethyl thioglycolate, cysteine, 2-mercaptoethanol, 1,3-mercaptopropanol, 3-mercaptopropane-1,2-diol, 1,4-mercaptobutanol, mercaptoacetic, 3-mercaptopropionic and mercaptosuccinic acids, thioglycerol, diethanol sulfide, thiodiglycol, ethylthioethanol, thiourea and dimethyl sulfoxide. Further suitable regulators are allyl compounds, such as allyl alcohol or allyl bromide, benzyl compounds, such as benzyl chloride, or alkyl halides, such as chloroform, bromotrichloromethane or tetrachloromethane. In a preferred embodiment the regulator is metered in into the reaction mixture as it is or as a solution in water and/or a $C_1$–$C_4$ alcohol.

The process of the invention is carried out if desired using the surface-active substances customary for an emulsion polymerization, in other words emulsifiers and/or protective colloids. Surface-active substances, where used, are employed in general in amounts of up to 20% by weight, preferably from 0.5 to 10% by weight and, in particular from 1 to 5% by weight, based on the monomers to be polymerized. Suitable surface-active compounds include both protective colloids and neutral, anionic or cationic emulsifiers. Suitable anionic emulsifiers include, in particular, the alkali metal or ammonium salts of relatively long-chain fatty acids, of sulfuric monoesters of ethoxylated fatty alcohols (EO units: 4 to 30, alkyl: $C_{10}$–$C_{22}$) and ethoxylated alkylphenols (EO units: 3 to 50, alkyl: $C_4$–$C_{10}$), of alkylsulfonic acids (alkyl: $C_{12}$–$C_{18}$) and of alkylarylsulfonic acids (alkyl: $C_9$–$C_{18}$). Further anionic emulsifiers which can be used are the alkali metal salts of sulfosuccinic acid dialkyl esters, and the alkali metal salts of the sulfonic acids of alkylnaphthalenes and of naphthalene itself. It is also possible to use cation-active compounds, such as quaternary fatty amines, quaternary alkyl pyridines (alkyl: $C_8$–$C_{30}$), quaternary N-alkylmorpholines (alkyl: $C_8$–C30) or alkylated imidiazolines.

Additional auxiliaries with an emulsifying action (cosolvents) can be added together with the emulsifiers in amounts of up to 20% by weight, preferably from 0.5 to 10% by weight and, in particular, from 1 to 5% by weight, based on the monomers. Suitable cosolvents embrace linear or branched aliphatic or cycloaliphatic $C_1$–$C_{30}$ alcohols or mixtures thereof, such as n-butanol, n-hexanol, cyclohexanol, 2-ethylhexanol, isooctanol, n-octanol, n-decanol, n-dodecanol, stearyl alcohol, oleyl alcohol and cholesterol. Further cosolvents are $C_4$–$C_{20}$-alkanediols, ethylene glycol alkyl ethers with 1 to 4 ethylene oxide units, such as ethylene glycol monobutyl ether, diethylene glycol monoethyl ether or tetraethylene glycol dimethyl ether, and N-alkylpyrrolidones, N-alkyl- and N,N-dialkylacetamides having 1 to 8 carbons in each alkyl chain, examples being N-methylpyrrolidone, N-hexylpyrrolidone, diethylacetamide and N-octylacetamide.

The process of the invention is particularly suitable for preparing aqueous polymer dispersions comprising from 20 to 60% by weight and in particular from 30 to 60% by weight of monomers A in copolymerized form, based on the overall amount of monomers to be polymerized. The monomers A are preferably N-vinyllactams of 6 to 8 carbons, such as N-vinylpyrrolidone, N-vinylpiperidone, N-vinylcaprolactam, and/or acrylic N-vinylcarboxamides of 2 to 6 carbons, such as N-vinylformamide or N-methyl-N-vinylacetamide. Particularly preferred monomers A are the N-vinyllactams. N-Vinylimidazole is likewise suitable as a monomer A. In a preferred embodiment of the present invention the water-solubility of the monomer A is >100 g/l (at 25° C.).

Suitable monomers B are in principle all hydrophobic monomers having a water-solubility of less than 60 g/l at 25° C. which are copolymerizable with the monomers A. They include, in particular, the $C_1$–$C_{10}$-alkyl esters of monoethylenically unsaturated $C_3$–$C_6$ carboxylic acids, especially the esters of acrylic and methacrylic acid with $C_1$–$C_{10}$-alkanols or $C_5$–$C_{10}$4-cycloalkanols such as methanol, ethanol, n-propanol, isopropanol, n-butanol, isobutanol, 2-butanol, tert-butanol, n-pentanol, n-hexanol, 2-ethylhexan-1-ol, n-octanol, n-decanol, 2-propylheptan-1-ol, cyclohexanol, 4-tert-butylhexanol, or 2,3,5-trimethylcyclohexanol. Further suitable monomers B are the di-$C_1$–$C_{10}$-alkyl esters of ethylenically unsaturated dicarboxylic acids, such as maleic, fumaric or itaconic acid, with the abovementioned $C_1$–$C_{10}$-alkanols or $C_5$-$C_{10}$-cycloalkanols, examples being dimethyl maleate or di-n-butyl maleate. Vinlyaromatic compounds such as styrene and α-methylstyrene are also suitable as monomers B, and their aromatic ring may be unsubstituted or substituted by one or more substituents selected from $C_1$–$C_4$-alkyl, halo, especially choro, and/or hydroxyl, which in its turn may also be ethoxylated. The monomers B additionally embrace the vinyl, allyl and methallyl esters of linear or branched aliphatic carboxylic acids of 2 to 20 carbons, such as vinyl acetate, propionate, butyrate, valerate, hexanoate, 2-ethylhexanoate, decanoate, laurate and stearate, and the corresponding allyl and methallyl esters. Suitable monomers B are in addition the vinyl, allyl and methallyl ethers of linear or branched aliphatic alcohols of 2 to 20 carbons, such as vinyl methyl, ethyl, dodecyl, hexadecyl and stearyl ethers. The monomers B are preferably used in amounts of from 40 to 70% by weigh and, in particular, from 40 to 60% by weight.

Suitable monomers C, which carry at least one ionic and/or ionizable functional group, include both anionic or acidic monomers and cationic monomers. The monomers C are preferably used in amounts of up to 5% by weight and, in particular, up to 3% by weight, based in the case of the acidic monomers on the free acid. Suitable anionic or acidic monomers include, in particular, those compounds that have at least one carboxyl, sulfo and/or phosphono group in the molecule. Suitable anionic and, respectively, acidic monomers include ethylenically unsaturated $C_3$–$C_6$ monocarboxylic acids, such as acrylic, methacrylic or crotonic acid, ethylenically unsaturated $C_4$–$C_8$ dicarboxylic acids, such as maleic, fumaric, itaconic or methylenemalonic acid, and the monoesters of said $C_4$–$C_8$ dicarboxylic acids with $C_1$–$C_{10}$-alkanols, such as monomethyl maleate, mono-n-butyl maleate; ethylenically unsaturated sulfonic acids such as vinylsulfonic, stryenesulfonic, 2-acrylamido-3-methylpropanesulfonic and 2-methacrylamido-2-methylpropanesulfonic acid, and ethylenically unsaturated phosphonic acids, such as vinylphosphonic acid. Said acids are preferably employed in their salt form suitable counterions include ions of alkali metals and alkaline earth metals, such as sodium, potassium or calcium, and ammonium ions. In a preferred embodiment of the present invention the free acids are converted, prior to the polymerization, into the anionic form with the aid of an appropriate base, preferably in the form of an aqueous or aqueous-alcoholic solution. Suitable bases include the hydroxides and carbonates of the abovementioned alkali metals, calcium hydroxide, ammonia and organic amines, pyridines and amidines. Suitable organic amines include, in particular, mono-, di- or trialkanolamines having 2 to 5 carbons in the alkanol radical, such as mono-, di- or triethanolamine, mono-, di- or tri(iso) propanolamine or 2-amino-2-methylpropanol; alkanediolamines with 2 to 4 carbons in the alkanediol radical, such as 2-amino-2-methyl-1,3-propanediol or 2-amino-2-ethyl-1,3-propanediol; alkanepolyamines, such as di(2-ethylhexyl)-amine, triamylamine or dodecylamine, and amino ethers, such as morpholine.

Suitable cationic monomers C include ethylenically unsaturated, nitrogen-basic compounds, examples being N-vinylimidazoles such as N-vinylimidazole, 2-methyl-1-vinylimidazole, 2-ethyl-1-vinylimidazole, 4-methyl-1-vinylimidazole or 5-methyl-N-vinylimidazole, N-vinylimidazolines, 2-, 3- or 4-vinylpyridine, which have been converted into the quaternary form by alkylation.

Suitable alkylating agents comprise alkyl halides, such as methyl chloride, bromide and iodide, ethyl chloride, propyl chloride, benzyl chloride or benzyl bromide; also dialkyl sulfates, especially dimethyl or diethyl sulfate, and alkylene oxides, such as ethylene oxide or propylene oxide, in the presence of acids. Preferred alkylating agents are methyl chloride, dimethyl sulfate and diethyl sulfate. The cationic monomers C also include diallylammonium compounds, such as dimethyldiallylammonium chloride, diethylallylammonium chloride or diallylpiperidinium bromide. Further possible compounds for use as cationic monomers C are the esters of ethylenically unsaturated $C_3$–$C_6$ carboxylic acids with aminoalkanols of the formula I or the amides of the ethylenically unsaturated carboxylic acids with amines of the formula II

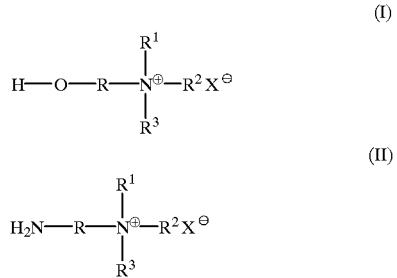

where R is $C_2$–$C_5$-alkylene, $R^1$, $R^2$, and $R^3$ independently of one another are $CH_3$, $C_2H_5$ or $C_3H_7$ and $X^\ominus$ is the anion of a mineral acid, such as chloride, the anion of a carboxylic acid, or is methosulfate or ethosulfate.

The polymer dispersions of the invention can also be prepared using what are known as crosslinking monomers, D, in other words monomers having at least two ethylenically unsaturated bonds. Particularly suitable monomers D encompass the di- or polyesters of dihydric or higher polyhydric alcohols with ethylenically unsaturated $C_3$–$C_6$ carboxylic acids. Examples of such compounds are alkylene glycol diacrylates and dimethacrylates, such as ethylene glycol di(meth)acrylate, 1,3- or 1,4-butylene glycol di(meth)acrylate, diethylene glycol di(meth)acrylate, 1,6-hexanediol di(meth)acrylate, neopentyl glycol di(meth)acrylate, triethylene glycol di(meth)acrylate, tetraethylene glycol di(meth)acrylate, 1,12-dodecanediol di(meth)acrylate, polyethylene glycol di(meth)acrylate, 2,2-bis(p-(meth)acryloxyphenyl) propane, tripropylene glycol di(meth)acrylate, trimethylolpropane tri(meth)acrylate, pentaerythritol tri(meth)acrylate or pentaerythritol tetra(meth)acrylate. Further suitable monomers D are the vinyl, allyl and methallyl esters of ethylenically unsaturated $C_3$–$C_6$ carboxylic acids, such as vinyl, allyl and methallyl (meth)acrylate, the vinyl, allyl and methallyl esters of aliphatic or aromatic dicarboxylic acids, such as divinyl phthalate or diallyl phthalate, polyfunctional amides of ethylenically unsaturated carboxylic acids, especially N,N'-methylenebisacrylamide, N,N'-butylidenebisacrylamide, bis(acrylamido)acetic acid methyl ester, and terephthalylidenetetraacrylamide. Further compounds which come into consideration as monomers D are divinylaromatic compounds, such as divinylbenzene, and also divinyl, diallyl or dimethallyl derivatives of urea and/or of imidazolidone, such as N,N'-divinylurea and N,N'-divinylimidazolidin-1-one. The monomers D are preferably used in amounts of up to 5% by weight and, preferably, up to 2% by weight.

Suitable monomers E are neutral water-soluble monomers containing no N-vinyl group. They include acrylonitrile, the hydroxyalkyl esters of the abovementioned $C_3$–$C_6$ carboxylic acids, such as hydroxyethyl, 2- or 3-hydroxypropyl or 4-hydroxybutyl (meth)acrylate, the amides and N-methylolamides of ethylenically unsaturated $C_3$–$C_6$ carboxylic acids, such as acrylamide and methacrylamide, and also the anhydrides of ethylenically unsaturated $C_4$–$C_6$ dicarboxylic acids, such as maleic anhydride. The monomers E are preferably used in amounts of up to 10% by weight.

In a preferred embodiment of the present invention, the polymerization is conducted in the absence of the monomers C. Accordingly, the mixture of monomers to be polymerized has the following composition:

from 10 to 70% by weight, preferably from 20 to 60% by weight and, in particular, from 30 to 60% by weight of monomers A from 30 to 90% by weight, preferably from 40 to 80% by weight and, in particular, from 40 to 70% by weight of monomers B from 0 to 10% by weight, preferably less than 5% by weight and, in particular, less than 2% by weight of crosslinking monomers D from 0 to 20% by weight, in particular less than 10% by weight and, with particular preference, no further, water-soluble monomers E which are different from the monomers A.

With very particular preference the monomer mixture to be polymerized in this embodiment contains only monomers A and B.

In this case the polymers can be prepared in either the presence or absence of surface-active compounds. Their absence is generally preferred, especially when the solubility of the hydrophobic monomers B in water is more than 10 g/l. Where necessary for the intended application, however, monomer mixtures of this type can also be polymerized in the presence of the abovementioned emulsifiers and/or protective colloids.

In another embodiment of the present invention the monomers A and B and, if used, the monomers D and E are polymerized in the presence of ionic or ionizable monomers C. Preference is given to the use of from 0.1 to 10% by weight, in particular from 0.2 to 5% by weight and, with particular preference, from 0.5 to 3% by weight, of monomers C, based on the overall amount of the monomers to be polymerized. The monomers C stabilize the polymers, thus obviating the need to use emulsifiers and/or protective colloids in the course of the emulsion polymerization. Where desired for the intended application, however, such surface-active compounds can be added to the polymerization reaction in the amounts indicated above. Despite this possibility, preference is given to the surfactant-free preparation process. The amounts of the monomers A, B, D and E are subject to the comments made above. Preferred monomer mixtures in the case of this embodiment contain only the monomers A to C.

The polymer dispersions obtainable by the process of the invention are novel and are likewise provided by the present invention. The solids content of such polymer dispersions is usually within the range from 10 to 60% by weight, preferably from 15 to 40% by weight, based on the overall weight of the dispersion. The light transmittance of the polymer dispersions that are obtainable in accordance with the invention (based on a 0.5% by weight dilution with a path length of 1 cm) is generally above 50% and preferably above 70%. The particle size of the dispersed polymer particles is generally more than 50 nm and preferably more than 100 nm. The parameter chosen to be used here is the ponderal median of the particle size, as can be determined using an analytical ultracentrifuge in accordance with the methods of W. Scholtan and H. Lange, Colloid-Z. und Z. Polymere 250 (1972) 782–796.

The polymers that are obtainable in accordance with the invention generally have high molecular weights, corresponding to 45 Fikentscher K values (H. Fikentscher, Zellulose-Chemie, Volume 13, (1932) 58–64; measured as a 1% strength by weight solution of the polymer in ethanol) of more than 50, preferably more than 70 and, with particular preference, more than 80. Through the use of regulators it is also possible to establish lower molecular weights. Even in such cases the weight-average molecular weight M is generally >50,000, corresponding to Fikentscher K values of more than 30.

The polymer dispersions obtain able by the process of the invention can if required be converted to solid powders by a prior art drying process. Other than freeze drying, suitable drying processes include, in particular, spray drying, fluidized-bed spray drying, roller drying and belt drying. For a range of applications it is advisable to convert the aqueous polymer dispersions into solid forms with the aid of evaporative extruders.

The polymers obtained by the process of the invention on the one hand act as thickeners in the aqueous medium and on the other hand are able to form water-soluble films. They can be used as auxiliaries for pharmaceutical, cosmetic or agrochemical formulations and for producing paints and coating compositions, sizes and adhesives. In particular they are employed in cosmetic and pharmaceutical formulations, for instance as additives or vehicles in hair lacquers, hair-setting products or hair sprays; in cosmetic preparations for the skin, as skin-adhering gels or as immunochemicals—as catheter coatings, for example. Specific pharmaceutical applications of the polymers of the invention include, in particular, their use as wet or dry binders, release-slowing agents in the matrix or coating of slow-release dosage forms, gel formers, instant-release coatings, and film-coating auxiliaries. The polymers prepared in accordance with the invention can also be used as auxiliaries for agrochemicals; for example, for seed coating or in soil-release fertilizer formulations, or as auxiliaries in the production of granular fish foods.

By virtue of the strong dispersing action of the polymers prepared in accordance with the invention, both for organic and inorganic pigments, the polymers of the invention are suitable as agents for preventing or removing rust on metallic surfaces, for preventing or removing scale, as dispersants in dye/pigment dispersions, as for example in printing inks. In this context reference may be made to the use of the polymers of the invention for inkjet recording media, writing-ink pastes and ballpoint pen pastes.

Also of interest from an applicational standpoint is the high propensity of the polymers of the invention to form complexes with organic compounds (for example, lower hydrocarbons, phenols, tannin and various antioxidants), with enzymes and proteins, or with other organic polymers. The polymers of the invention also form complexes with inorganic compounds, especially with hydrogen peroxide, halides, metals or metal salts. The polymers of the invention can be used accordingly to remove tannin, phenols, proteins or polyvalent cations from an aqueous medium, in ion exchangers, to stabilize hydrogen peroxide in disinfectants, for example, to stabilize antioxidants, in preservatives, for example, as a polymeric coligand for metal complexes in the reversible absorption of oxygen, or catalysts. The polymers of the invention can additionally be used to stabilize metal colloids. In this context reference may also be made to the use of the polymers of the invention as noble metal crystallization nuclei for the precipitation of silver, and as a stabilizer for silver halide emulsions.

The polymers of the invention also show suitability for modifying surface and interface properties. On the basis of their modifying action for surfaces the products of the invention can be used as coatings for polyolefins, for example, and for glass and for glass fibers. Owing to their surface activity they are also used as protective colloids in connection, for example, with the stabilization of metal colloids or with free-radical aqueous emulsion polymerization. In this context reference may also be made to the use of the polymers of the invention as auxiliaries in the recovery of petroleum from oil-containing water, as auxiliaries in the extraction of petroleum and natural gas, and in the transportation of petroleum and natural gas. Other areas where the polymers of the invention find application are as assistants in the purification of wastewaters, whether as flocculation aids or in the removal of paint and oil residues from wastewater. The polymers of the invention can also be used as phase transfer catalysts and as solubility enhancers.

The polymers of the invention are also used in the coloring of polyolefins, as color mixing inhibitors for photographic diffusion transfer materials, as adhesion promoters for dyes, as auxiliaries in lithography, photoimaging and the diazotype process, as auxiliaries for the casting and tempering of metal, as auxiliaries for metal quenching baths, as auxiliaries in gas analysis, as a constituent of ceramic binders, as papermaking aids for specialty papers, as binders in colored paper slips, and as a binder constituent in plaster bandages.

The polymers of the invention are suitable, furthermore, as proton conductors and can be used in electroconductive layers in connection, for example, with charge transfer cathodes, and as solid electrolytes, in solid batteries such as lithium batteries, for example. The polymers of the invention can be used to produce contact lenses, synthetic fibers, air filters, for example cigarette filters, or membranes. The polymers of the invention also find application in heat-resistant layers, heat-sensitive layers and heat-sensitive resistors.

The examples set out below are intended to illustrate the invention without restricting it.

EXAMPLES

I. Analysis

The polymers were characterized by viscometric determination of their K value in the manner described by H. Fikentscher (see H. Fikentscher, Zellulose-Chemie 13 (1932) 58–64 and 71–74, and in Encyclopedia of Chemical Technology, 2nd edition, Kirk Othmer, Wiley & Sons, 1970, pp. 427–428). This was done by drying a sample of the respective dispersion and, from the polymer, preparing a 1% strength by weight solution in ethanol.

The light transmittance was determined by diluting a sample of the respective dispersion with deionized water to a solids content of 0.5% by weight and then measuring the optical transmittance over a path length of 1 cm.

The residual monomer content was determined by gas chromatography

II. Preparing the Copolymer Dispersions of the Invention (Examples 1 to 20)

Example 1

Dispersion comprising 30% by weight N-vinylpyrrolidone and 70% by weight vinyl acetate.

A reactor with stirrer, reflux condenser, gas inlet and two separate feed ports was charged with a mixture of

| |
|---|
| 20 g of N-vinylpyrrolidone, |
| 50 g of vinyl acetate, |
| 5 g of initiator feed stream 1, and |
| 1000 g of water. |

This initial charge was flushed with nitrogen and heated to an internal temperature of 70° C. Subsequently, while maintaining the temperature, the monomer feed stream and the initiator feed stream 1 were added simultaneously and at a constant rate over a period of 8 hours. In the course of polymerization the reaction solution was adjusted to a pH of 6–7 using dilute ammonia solution. The internal temperature was then raised to 75° C. and the initiator feed stream 2 was added over a period of 6 hours while maintaining this temperature. The temperature was held at 75° C. for 2 hours more. The reaction mixture was subsequently subjected to steam distillation. About 100 g of distillate were collected, and the solids content was adjusted to about 20% by weight. This gave a white, sedimentation-stable dispersion having a K value of 95, a solids content of 19.5% by weight and a residual monomer content of 130 ppm of N-vinylpyrrolidone. A sample concentrated by evaporation gave a clear solution in ethanol.

| | |
|---|---|
| Monomer feed stream: | 70 g of N-vinylpyrrolidone, |
| | 160 g of vinyl acetate |
| Initiator feed stream 1: | Solution of 1 g of |
| | 2,2'-azobis(2-amidinopropane) |
| | dihydrochloride in 100 g of water |
| Initiator feed stream 2: | Solution of 1 g of |
| | 2,2'-azobis(2-amidinopropane) |
| | dihydrochloride in 100 g of water |

The pH of the initial charge and of the initiator feed streams 1 and 2 was adjusted to 6 using dilute ammonia solution.

Example 2

Dispersion comprising 30% by weight N-vinylpyrrolidone and 70% by weight vinyl acetate.

A reactor with stirrer, reflux condenser, gas inlet and two separate feed ports was charged with a mixture of

| |
|---|
| 20 g of N-vinylpyrrolidone, |
| 50 g of vinyl acetate, |
| 6 g of ammonium hydrogen carbonate, |
| 5 g of initiator feed stream 1, and |
| 1000 g of water. |

The polymerization procedure is the same as that of Example 1. In the course of polymerization the pH of the reaction solution is kept constant (pH 5–7) by adding buffer (ammonium hydrogencarbonate). This gave a white, sedimentation-stable dispersion having a K value of 98, a solids content of 19.7% by weight and a residual monomer content of 70 ppm of N-vinylpyrrolidone. A sample concentrated by evaporation gave a clear solution in ethanol.

| | |
|---|---|
| Monomer feed stream: | 70 g of N-vinylpyrrolidone, |
| | 160 g of vinyl acetate |

Initiator feed streams 1 and 2 are the same as those of Example 1.

Example 3

Dispersion comprising 30% by weight N-vinylpyrrolidone and 70% by weight vinyl acetate (regulated procedure).

The polymerization was performed as described in Example 1. In deviation from Example 1, the monomer feed stream additionally contained 2 g of allyl alcohol.

This gave a white, sedimentation-stable dispersion with a pale yellowish discoloration, having a K value of 72, a solids content of 19.1% by weight and a residual monomer content of 550 ppm of N-vinylpyrrolidone. A sample concentrated by evaporation gave a clear solution in ethanol.

Example 4

Dispersion comprising 30% by weight N-vinylpyrrolidone and 70% by weight vinyl acetate (regulated procedure).

The polymerization was performed as described in Example 1. In deviation from Example 1, the monomer feed stream additionally contained 0.5 g of mercaptoethanol. This gave a white, sedimentation-stable dispersion with a pale yellowish discoloration, having a K value of 72, a solids content of 19.1% by weight and a residual monomer content of 550 ppm of N-vinylpyrrolidone. A sample concentrated by evaporation gave a clear solution in ethanol.

Example 5

Dispersion comprising 20% by weight N-vinylpyrrolidone and 80% by weight vinyl acetate (regulated procedure).

A reactor with stirrer, reflux condenser, gas inlet and two separate feed ports was charged with a mixture of

| |
|---|
| 15 g of N-vinylpyrrolidone, |
| 50 g of vinyl acetate, |
| 5 g of initiator feed stream 1, and |
| 1000 g of water. |

The polymerization procedure and the initiator feed streams 1 and 2 are the same as those of Example 1. This gave a white, sedimentation-stable dispersion having a K value of 61, a solids content of 20.3% by weight and a residual monomer content of 200 ppm of N-vinylpyrrolidone. A sample concentrated by evaporation gave a clear solution in ethanol.

| | |
|---|---|
| Monomer feed stream: | 45 g of N-vinylpyrrolidone, |
| | 190 g of vinyl acetate, |
| | 2 g of allyl alcohol. |

Initiator feed streams 1 and 2 are the same as those of Example 1.

Example 6

Dispersion comprising 60% by weight N-vinylpyrrolidone and 40% by weight tertiary-butyl acrylate (anionic product).

A reactor with stirrer, reflux condenser, gas inlet and three separate feed ports was charged with a mixture of 50 g of N-vinylpyrrolidone,
0.6 g of 0.01% strength by weight $Cu^{II}Cl_2$ solution
5 g of initiator feed stream 1, and
1000 g of water.

This initial charge was heated to 70° C. under nitrogen, and the monomer feed streams 1 and 2 and initiator feed stream were added simultaneously and at a constant rate over a period of 8 hours. The temperature was subsequently held at 75° C. for 6 hours more. This gave a white, sedimentation-stable dispersion having a K value of 78, a solids content of 19.4% by weight and a residual monomer content of 50 ppm of N-vinylpyrrolidone. A sample concentrated by evaporation gave a clear solution in ethanol.

| Monomer feed stream 1: | 130 g of N-vinylpyrrolidone, 120 g of tertiary-butyl acrylate |
|---|---|
| Monomer feed stream 2: | 3.0 g of acrylic acid neutralized with sodium hydroxide, 50 g of water |
| Initiator feed stream: | Solution of 10 g of hydrogen peroxide (30% by weight) in 50 g of water. |

Example 7

Dispersion comprising 60% by weight N-vinylpyrrolidone and 40% by weight tertiary-butyl acrylate (anionic product).

The polymerization procedure and the monomer feed streams are the same as those of Example 6, and the initiator feed stream contained 20 g of hydrogen peroxide solution (30% by weight) dissolved in 50 g of water. This gave a white, sedimentation-stable dispersion having a K value of 62, a solids content of 20.0% by weight and a residual monomer content of <50 ppm of N-vinylpyrrolidone. A sample concentrated by evaporation gave a clear solution in ethanol.

Example 8

Dispersion comprising 60% by weight N-vinylpyrrolidone and 40% by weight tertiary-butyl acrylate (regulated procedure).

A reactor with stirrer, reflux condenser, gas inlet and two separate feed ports was charged with a mixture of 50 g of N-vinylpyrrolidone,
5 g of initiator feed stream 1, and
1000 g of water.

The polymerization procedure is the same as that of Example 1. This gave a white, sedimentation-stable dispersion having a K value of 79, a solids content of 19.9% by weight and a residual monomer content of 70 ppm of N-vinylpyrrolidone. A sample concentrated by evaporation gave a clear solution in ethanol.

| Monomer feed stream: | 130 g of N-vinylpyrrolidone, 120 g of tertiary-butyl acrylate, 1 g of mercaptoethanol |
|---|---|
| Initiator feed stream 1: | Solution of 1 g of 2,2'-azobis(2-amidinopropane) dihydrochloride and 3.0 g of acrylic acid, neutralized with sodium hydroxide, in 100 g of water |
| Initiator feed stream 2: | Solution of 1 g of 2,2'-azobis(2-amidinopropane) dihydrochloride in 100 g of water. |

Example 9

Dispersion comprising 60% by weight N-vinylpyrrolidone and 40% by weight of tertiary-butyl acrylate (regulated procedure).

The polymerization procedure, the monomer feed streams and the initiator feed stream are the same as those of Example 8, with the monomer feed stream containing 9 g of mercaptoethanol. This gave a white, sedimentation-stable dispersion having a K value of 50, a solids content of 19.0% by weight and a residual monomer content of <50 ppm of N-vinylpyrrolidone. A sample concentrated by evaporation gave a clear solution in ethanol.

Example 10

Dispersion comprising 60% by weight N-vinylpyrrolidone and 40% by weight tertiary-butyl acrylate (cationic product).

A reactor with stirrer, reflux condenser, gas inlet and two separate feed ports was charged with a mixture of 50 g of N-vinylpyrrolidone,
5 g of initiator feed stream 1, and
1000 g of water.

The polymerization procedure is the same as that of Example 1. This gave a white, sedimentation-stable dispersion having a K value of 38, a solids content of 20.3% by weight and a residual monomer content of 300 ppm of N-vinylpyrrolidone. A sample concentrated by evaporation gave a clear solution in ethanol.

| Monomer feed stream: | 121 g of N-vinylpyrrolidone, 120 g of tertiary-butyl acrylate |
|---|---|
| Initiator feed stream 1: | Solution of 1 g of 2,2'-azobis(2-amidinopropane) dihydrochloride and 9.0 g of 3-methyl-1-vinylimidazolium methyl sulfate (methosulfate), as a neutralized solution, in 100 g of water |
| Initiator feed stream 2: | Solution of 1 g of 2,2'-azobis( 2-amidinopropane) dihydrochloride in 100 g of water. |

Example 11

Dispersion comprising 60% by weight N-vinylformamide and 40% by weight tertiary-butyl acrylate (anionic product).

A reactor with stirrer, reflux condenser, gas inlet and two separate feed ports was charged with a mixture of

| | |
|---|---|
| 50 g of N-vinylformamide, | |
| 5 g of initiator feed stream 1, and | |
| 1000 g of water. | |

The polymerization procedure is the same as that of Example 1. This gave a white, sedimentation-stable dispersion having a K value of 56, a solids content of 19.4% by weight and a residual monomer content of 350 ppm of N-vinylpyrrolidone. A sample concentrated by evaporation gave a clear solution in ethanol.

| Monomer feed stream: | 130 g of N-vinylformamide, 120 g of tertiary-butyl acrylate |
|---|---|
| Initiator feed stream 1: | Solution of 1 g of 2,2'-azobis(2-amidinopropane) dihydrochloride and 3.0 g of acrylic acid, neutralized with sodium hydroxide in 100 g of water |
| Initiator feed stream 2: | Solution of 1 g of 2,2'-azobis(2-amidinopropane) dihydrochloride in 100 g of water. |

Example 12

Dispersion comprising 40% by weight N-vinylpyrrolidone and 60% by weight tertiary-butyl methacrylate (emulsifier-containing dispersion).

A reactor with stirrer, reflux condenser, gas inlet and two separate feed ports was charged with a mixture of 10 g of Texapon® NSO (ethoxylated sodium lauryl sulfate)

2.2 g of sodium peroxodisulfate, 7% strength solution in water 0.8 g of ammonium hydrogencarbonate, 20 g of monomer feed stream, and 750 g of water.

This initial charge was flushed with nitrogen and heated to an internal temperature of 80° C. Subsequently, while maintaining the temperature, the monomer feed stream and the initiator feed stream 1 were added simultaneously and at a constant rate over a period of 2 hours. The temperature was held at 80° C. for 2 hours more. Then initiator feed stream 2 was added and the temperature was maintained at 80° C. for one hour more; following the addition of initiator feed stream 3, the temperature was held at 80° C. for a further 3 hours.

This gave a white, sedimentation-stable dispersion having a K value of 48, a solids content of 28.8% by weight, a light transmittance of 70.5%, a pH of 8.2 and a residual monomer content of 1500 ppm of N-vinylpyrrolidone. A sample concentrated by evaporation gave a clear solution in ethanol.

| Monomer feed stream: | 180 g of tertiary-butyl methacrylate, 120 g of N-vinylpyrrolidone, 0.6 g of 2-ethylhexyl thioglycolate (EHTG). |
|---|---|
| Initiator feed stream 1: | 9 g of sodium peroxodisulfate, 7% strength solution in water. |
| Initiator feed stream 2: | 3.0 g of hydrogen peroxide (30% strength solution) 0.5 g of Cu$^{II}$Cl$_2$ (0.01% strength solution in water) |
| Initiator feed stream 3: | 1.5 g of hydrogen peroxide (30% strength solution). |

Examples 13 to 20

Emulsifier-containing Dispersions

Polymerization was carried out as in Example 12. The amounts of monomers employed and their characteristics are summarized in Table 1. For the monomers, the following abbreviations have been used:

VP=N-vinylpyrrolidone

VC=N-vinylcaprolactam t-BuMA=tert-butyl methacrylate i-BuMA=isobutyl methacrylate MMA=methyl methacrylate

TABLE 1

| Ex. | Monomers A [g] | B [g] | Regulator (EHTG)[1] [g] | K value[2] | LT[3] [%] | SC[4] [% by wt.] | pH | Residual monomers [ppm] |
|---|---|---|---|---|---|---|---|---|
| 13 | VP 120 | t-BuMA 180 | 1.1 | 41 | 63.5 | 30.6 | 7.0 | VP 2000 |
| 14 | VP 60 | t-BuMA 240 | 0.6 | 45 | 66.5 | 32.1 | 7.6 | VP 2000 |
| 15 | VP 60 | MMA 240 | 0.6 | 47 | 82.0 | 33.1 | 7.8 | VP 500 |
| 16 | VC 90 | t-BuMA 210 | 0.6 | 54 | 77.0 | 28.7 | —[5] | VC 200 |
| 17 | VC 90 | t-BuMA 210 | 1.1 | 38 | 73.5 | 28.6 | — | VC 500 |
| 18 | VC 120 | t-BuMA 180 | 1.1 | 44 | 93.0 | 28.3 | — | VC 60 |
| 19 | VC 90 | i-BuMA 210 | 1.1 | 43 | 67.5 | 35.2 | — | VC 100 |
| 20 | VC 60 | MMA 240 | 1.1 | 47 | 76.0 | 28.6 | — | VC 300 |

[1]EHTG: 2-ethylhexyl thioglycolate
[2]Fikentscher K value (see above)
[3]LT: light transmittance of a 1% strength dispersion (see above)
[4]SC: solids content
[5]Value not determined III. Use of the Polymers of the Invention as Film Formers in Hairsprays Example 21

The polymer dispersions of Examples 5, 9, 10 and 13 were converted to a polymer powder in a known method, by spray drying.

3 g of copolymer were dissolved in 62 g of ethanol and 35 g of dimethoxyethane. The resulting hairspray formulations were tested on headforms and show excellent properties as hair cosmetics. Even without further additives they exhibit an excellent hairsetting effect. To further optimize the cosmetic properties the constituents known to the skilled worker can be added to the formulations.

IV. Use of the Polymers of the Invention as Release-slowing Agents for Use in Drug Coatings First of all a pigment dispersion comprising 0.5 part by weight of titanium dioxide powder 4.0 parts by weight of talc 0.5 part by weight of food dye (Sicovit® red 30) and 7.0 parts by weight of water was prepared and was homogenized in a corundum disk mill.

Then 58 parts by weight of water and 30 parts by weight of the dispersion from Example 1 were added. The resulting dispersion had a solids content of 11% by weight.

1745 g of this dispersion were applied by fluidized-bed spraying in an Aeromatic Strea 1 (from Aeromatic) to 500 g of theophylline pellets (0.8 to 1.3 mm, Spherofillin® from Knoll AG). The incoming air temperature was 45° C. and the outgoing air temperature 30° C. The rate of incoming air was 100–130 m$^3$/h. Spray application was carried out continuously for 205 minutes at a rate of 8.5 ml/min and at a spraying pressure of 0.8 bar. Drying then took place for 5 minutes in a stream of hot air (60° C.).

To determine the release, the coated pellets were packed in capsules (corresponding to 300 mg of theophilline per capsule) which were each introduced into 900 ml of simulated gastric fluid (0.1 N hydrochloric acid). Release was carried out in a paddle apparatus (from Pharmatest) at 37° C. and 50 rpm. After 2 hours, a phosphate buffer concentrate was added to establish a pH of 6.8.

The release results were as follows:

| | |
|---|---|
| 2 h | 30.5% |
| 4 h | 55.6% |
| 6 h | 80.3% |
| 8 h | 100.0% |

These release results denote the percentages of theophylline released, as determined by UV photometry.

What is claimed is:

1. A process for preparing an aqueous copolymer dispersion by free-radical aqueous emulsion polymerization of ethylenically unsaturated monomers which process comprises reacting a monomer mixture of
   i) more than 20% and up to 60% by weight of at least one nonionic monomer A having a water-solubility of more than 60 g/l at 25° C., and being selected from the group consisting of N-vinyllactams having from 6 to 8 carbon atoms, N-vinylformamide and N-methyl-N-vinylacetamide,
   ii) from 40 to 80% by weight of at least one monoethylenically unsaturated hydrophobic monomer B having a water-solubility of less than 60 g/l at 25° C., in the presence of a water-soluble polymerization initiator, said process being conducted as an emulsion polymerization in water or in a mixture of water and at least one $C_1$–$C_4$-alcohol, the alcohol being present in up to 20% by weight.

2. The process defined in claim 1, wherein the polymerization initiator is selected from water-soluble azo compounds, alkali metal of peroxodisulfuric acid, ammonium salts of peroxodisulfuric acid, and hydrogen peroxide.

3. The process defined in claim 1, wherein at least 70% of the initiator is supplied continuously to the polymerization reaction in the form of a solution in water or in a mixture of water and one or more $C_1$–$C_4$-alcohols.

4. The process defined in claim 1, wherein at least 70% by weight of the monomers are supplied to the polymerization reaction continuously.

5. The process defined in claim 1, wherein the monomers B are selected from a group consisting of olefins, vinylaromatic compounds, $C_1$–$C_{10}$-alkyl esters of monoethylenically unsaturated $C_3$–$C_6$-monocarboxylic acids, di-$C_1$–$C_{10}$-alkyl esters of ethylenically unsaturated $C_4$–$C_6$ dicarboxylic acids, vinyl and (meth)allyl esters of linear or branched aliphatic carboxylic acids of 2 to 20 carbon atoms, and vinyl and (meth)allyl ethers of linear or branched aliphatic alcohols of 2 to 20 carbon atoms.

6. The process defined in claim 1, wherein the monomer mixture comprises the monomers A in an amount of from 30 to 60% by weight.

7. The process defined in claim 1, wherein the polymerization is conducted in the absence of an emulsifier or a protective colloid.

8. An aqueous copolymer dispersion obtained by a process defined in claim 1.

9. The aqueous copolymer dispersion defined in claim 8 having a solids content of from 10 to 60% by weight.

10. The aqueous copolymer dispersion defined in claim 8 wherein the polymer particles have a weight-average diameter of more than 100 nm.

11. The aqueous copolymer dispersion defined in claim 8 wherein the copolymer has a Fikentscher K value of >50, measured as a 1% by weight solution in ethanol.

12. The aqueous copolymer dispersion defined in claim 11 wherein the copolymer has a Fikentscher K value of >70.

13. The aqueous copolymer dispersion defined in claim 8 having a solids content of from 15 to 40% by weight.

14. The process defined in claim 1, wherein the monomer mixture further comprises at least one monomer C having at least one ionic or ionizable functional group in an amount of from 0.1 to 10% by weight.

15. The process defined in claim 1, wherein the monomer mixture further comprises at least one monomer D having at least two ethylenically unsaturated bonds, in an amount of up to 10% by weight.

16. The process defined in claim 1, wherein the monomer mixture further comprises at least one monomer E having a water solubility of >60 g/l at 25° C., in an amount of up to 20% by weight, E being different from the monomers A.

17. The process defined in claim 15, wherein the monomer mixture further comprises at least one monomer E having a water solubility of >60g/l at 25° C., in an amount of up to 20% by weight, E being different from the monomers A and C.

18. The process defined in claim 15, wherein the monomer mixture further comprises the monomer D in an amount of less than 5% by weight.

19. The process defined in claim 15, wherein the monomer mixture further comprises the monomer D in an amount of less than 2% by weight.

20. The process defined in claim 15 wherein the monomer mixture consists essentially of the nonionic monomer or monomers A, the hydrophobic monomer or monomers B and the monomer or monomers D having at least two ethylenically unsaturated double bonds.

21. The process defined in claim 1, wherein at least one of the nonionic monomers A is N-vinylcaprolactam or N-vinylpyrrolidone.

22. The process defined in claim 1, wherein the nonionic monomer A is N-vinylcaprolactam or N-vinylpyrrolidone or a mixture of N-vinylcaprolactam and N-vinylpyrrolidone.

* * * * *